United States Patent
Naylor et al.

(10) Patent No.: US 7,902,810 B2
(45) Date of Patent: Mar. 8, 2011

(54) CABLE DETECTION SYSTEM

(75) Inventors: Thomas Kipling Naylor, Belmont, MA (US); Michael Naylor, legal representative, Belmont, MA (US); Clifford Risher-Kelly, Wells, ME (US); Charles LeMay, Portsmouth, NH (US)

(73) Assignee: Draeger Medical Systems, Inc., Andover, MA (US)

( * ) Notice: Subject to any disclaimer, the term of this patent is extended or adjusted under 35 U.S.C. 154(b) by 309 days.

(21) Appl. No.: 11/962,239

(22) Filed: Dec. 21, 2007

(65) Prior Publication Data

US 2009/0167286 A1   Jul. 2, 2009

Related U.S. Application Data

(60) Provisional application No. 60/871,249, filed on Dec. 21, 2006.

(51) Int. Cl.
  *G01R 19/00* (2006.01)
  *G01R 27/28* (2006.01)
  *H01R 9/05* (2006.01)

(52) U.S. Cl. ............ 324/66; 324/628; 439/489; 439/580

(58) Field of Classification Search .................. 324/66, 324/628; 439/488, 489, 578–580
See application file for complete search history.

(56) References Cited

U.S. PATENT DOCUMENTS

| 4,027,663 A | 6/1977 | Fischler et al. |
| 4,173,221 A | 11/1979 | McLaughlin et al. |
| 5,231,357 A | 7/1993 | Moody et al. |
| 5,260,659 A * | 11/1993 | Flowerdew et al. ............ 324/66 |
| 5,384,540 A | 1/1995 | Dessel |
| 5,559,427 A * | 9/1996 | Hinds et al. ..................... 324/66 |
| 5,629,628 A * | 5/1997 | Hinds et al. ..................... 324/66 |
| 5,649,001 A * | 7/1997 | Thomas et al. ............ 379/93.07 |
| 6,002,247 A | 12/1999 | Watkins |
| 6,385,297 B2 * | 5/2002 | Faulkner et al. .............. 324/525 |
| 6,530,085 B1 * | 3/2003 | Perlman ........................ 439/502 |
| 6,896,541 B2 * | 5/2005 | Benson ......................... 439/489 |
| 2007/0195167 A1 | 8/2007 | Ishiyama |
| 2007/0204174 A1 | 8/2007 | Dorogusker et al. |

FOREIGN PATENT DOCUMENTS

DE 19757823 A1  7/1999
EP  0721100 A2  7/1996

OTHER PUBLICATIONS

International Search Report dated Jun. 12, 2008, International Application No. PCT/US2007/088497.

* cited by examiner

*Primary Examiner* — Timothy J Dole
(74) *Attorney, Agent, or Firm* — Jack Schwartz & Associates, PLLC

(57) ABSTRACT

A cable detection system, includes a source of an input electrical AC signal for coupling to a first lead pin of a cable connector. A detector is coupled to a different second lead pin of the cable connector. The detector detects an electrical AC output signal derived by capacitive coupling of the input electrical AC signal occurring within a cable incorporating first and second leads corresponding to the first and second lead pins. The detector further enables a determination of whether the cable is connected to the cable connector in response to an amplitude dependent characteristic of the detected AC output signal.

17 Claims, 3 Drawing Sheets

CABLE DETECTION SYSTEM

CROSS-REFERENCED TO RELATED APPLICATIONS

This is a Non-Provisional application of U.S. Provisional Application Ser. No. 60/871,249 Filed Dec. 21, 2006.

FIELD OF THE INVENTION

The present invention relates generally to the field of electronic devices, and more particularly to the interconnection of electronic devices by means of removable, signal conducting cables.

BACKGROUND OF THE INVENTION

Electronic equipment often uses cables to attach to other electronic equipment, or to attach to transducers or other such electrodes, sensors or devices. In order to monitor such equipment and verify proper operation, it is sometimes required to detect that required cables have been attached. It is further sometimes required to detect the type of cables that have been attached.

For example, in the medical field, a patient monitoring system is often used in a healthcare facility in order to obtain information regarding selected physiological parameters of a patient. In such a system a multi-conductor cable is placed in the vicinity of the patient and patient data is gathered by one or more suitable sensors. The multi-conductor cable is plugged into or otherwise interconnected to the patient monitor so that that the gathered data may be usefully displayed. In order to ensure the integrity of the displayed data and/or to properly configure the displayed data, some means is needed to detect and verify the actual presence of the cable and the associated cable type. Among other benefits, detection of the type of cable would allow the patient monitoring system to allocate display area only for the particular physiological parameters that are obtained for the particular cable type.

In order to provide cable detection, known cable interconnection systems typically include one or more conductors that are dedicated to the cable detection function. Because the additional conductors reside within the cable, additional pins are required at the cable connector. However, in some situations the inclusion of additional conductors and connector pins may be either undesirable or impossible. For example, the additional pins needed within the connector may not be available. Other known systems use a mechanical switch or sensor to determine the presence of a cable. However, mechanical switches are cumbersome, expensive and eventually unreliable. In either case, in order to identify the type of cable that has been detected, one system requires that a separate coding resistor, having a standardized value, be included within the cable. Both types of known cable detection systems are not easily retrofitted into existing connector forms. A cable detection system constructed according to the principles of the present invention addresses these deficiencies and related problems.

BRIEF SUMMARY OF THE INVENTION

In accordance with principles of the present invention, a cable detection system, includes a source of an input electrical AC signal for coupling to a first lead pin of a cable connector. A detector is coupled to a different second lead pin of the cable connector. The detector detects an electrical AC output signal derived by capacitive coupling of the input electrical AC signal occurring within a cable incorporating first and second leads corresponding to the first and second lead pins. The detector further enables a determination of whether the cable is connected to the cable connector in response to an amplitude dependent characteristic of the detected AC output signal.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, cable detection system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by the display processor under the control of the processor. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to the processor. The processor, under control of the executable procedure or executable application manipulates the UI display images in response to the signals received from the input devices. In this way, the user interacts with the display image using the input devices, enabling user interaction with the processor or other device. A graphical user interface (GUI) uses graphical display images, as opposed to textual display images, when generating the UI.

Figure 1:
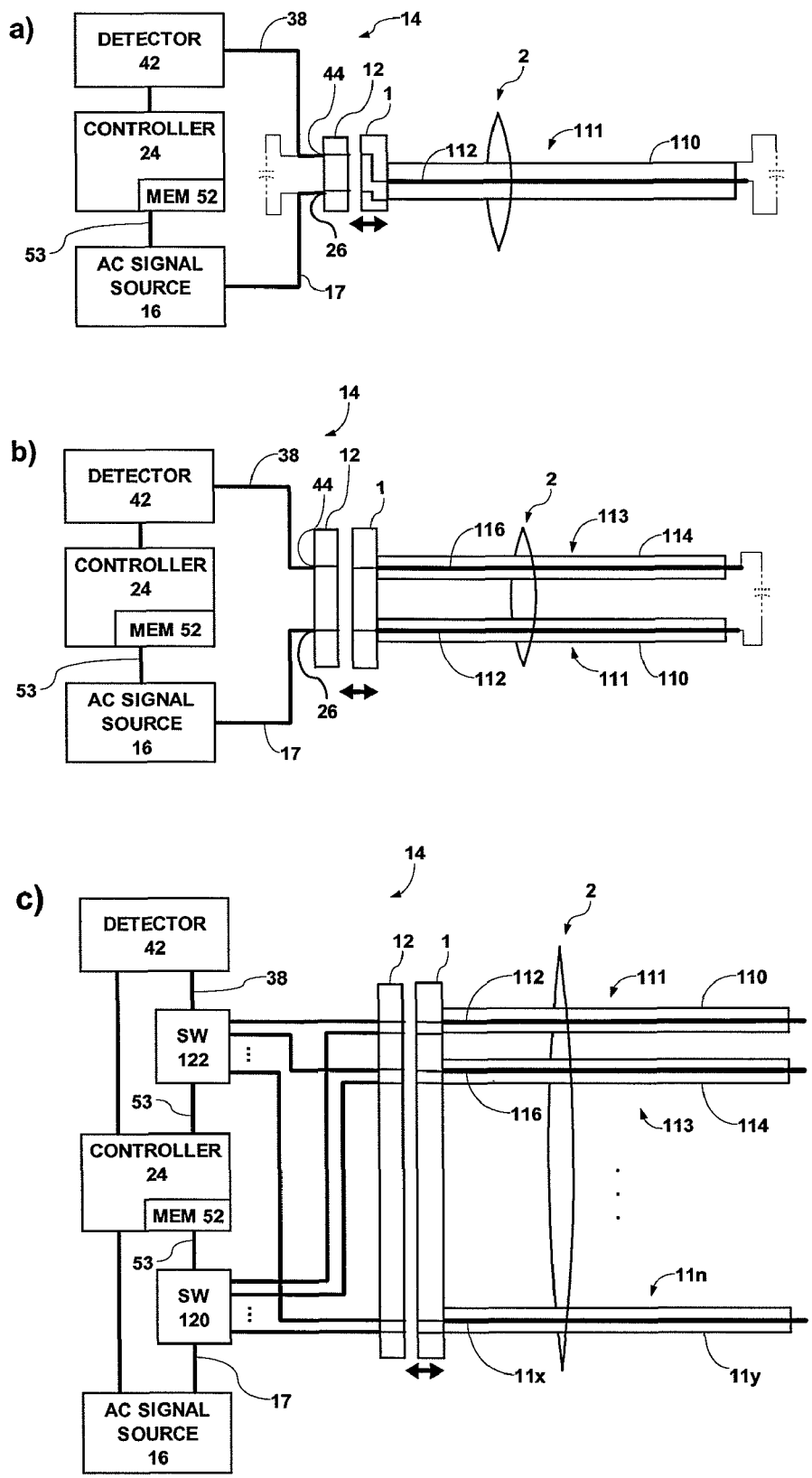
FIG. 1a, FIG. 1b and FIG. 1c illustrate respective embodiments of a portion of a system for detecting the presence of a cable in accordance with principles of the present invention.

FIG. 1a illustrates a portion of a system 14 for detecting the presence of a cable in accordance with principles of the present invention. The cable detection system 14 includes a source 16 of an input electrical AC signal 17. An output terminal of the AC signal source 16 is coupled to a first lead pin 26 of a cable connector 12. A detector 42 is coupled to a second lead pin 44 of the cable connector 12. The detector 42 detects an electrical AC output signal 38 derived by capacitive coupling of the input electrical AC signal 17 occurring within a cable 2 incorporating first and second leads (e.g. 110 and 112) corresponding to the first and second lead pins (e.g. 26 and 44, respectively). In FIG. 1a, the first and second leads (e.g. 110 and 112) are in the form of a coaxial cable 111. In the case illustrated in FIG. 1a, the first lead 110 is a shield conductor of the coaxial cable 111, and the second lead 112 is an inner conductor 112 of the coaxial cable 111. Alternatively, the second lead 112 may be a shield of a coaxial cable 111 and the first lead 110 may be an inner conductor of a coaxial cable 111.

The first and second leads (e.g. 110 and 112) are coupled to a cable plug 1 which connects them to the lead pins (e.g. 26 and 44, respectively) in the cable connector 12 when the cable plug 1 of the cable 2 is connected to the cable connector 12, as illustrated by the double arrow beneath the cable plug 1. The detector 42 enables a determination of whether the cable 2 is connected to the cable connector 12 in response to an amplitude dependent characteristic of the detected AC output signal 38.

In operation, the first and second leads (e.g. 110 and 112) of the cable 2 are capacitively coupled, as represented by a capacitor in phantom between the first and second leads (e.g. 110 and 112) at the right end of the cable 2. This capacitance, termed the characteristic capacitance, provides a path through which an AC signal, such as the AC input signal 17 received from the AC signal source 16, may pass from the first lead 110 to the second lead 112. There is also a capacitive coupling within the system 14, for example within the cable connector 12, represented by a capacitor in phantom from lead pin 44 to lead pin 26 of the cable connector 12. However, this capacitance is smaller than the capacitance between leads 110 and 112 in the cable 2 and consequently this impedance is larger than the impedance of the cable 2.

If the cable 2 is connected, then the input AC signal 17 from the AC signal source 16 is capacitively coupled from the first lead 110 to the second lead 112. The output AC signal 38 in the second lead 112 is detected by the detector 42. The detector 42 detects the amplitude of the received output AC signal 38 from the second lead 112. More specifically, the detector 42 determines whether the cable 2 is connected to the cable connector 12 in response to an amplitude dependent characteristic of the detected AC output signal 38 exceeding a predetermined threshold value. If the cable 2 is not connected, the AC signal from the first lead pin 26 is still capacitively coupled to the second lead pin 44 due to capacitive coupling within the system 14. But because the impedance is larger, the amplitude of the output AC signal 38 detected by the detector 42 is smaller. The difference in amplitude of the detected AC signal enables determination of whether the cable 2 is connected to the cable connector 12.

The system 14 further includes a controller 24 for automatically initiating generation of the input electrical AC signal 17 for coupling to the first lead 110, and for turning off the input electrical AC signal 17 after determination by the detector 42 of whether the cable 2 is connected to the cable connector 12. More specifically, the controller automatically synchronizes initiating generation of the input electrical AC signal 17, for coupling to the first lead 110, and detection by the detector 42 of whether the cable 2 is connected to the cable connector 12 in response to a timing signal 53 to avoid interference with other signals.

In operation, the controller 24 provides a control signal 53 to the AC signal source 16 conditioning the AC signal source 16 to produce the input AC signal 17 in order to detect the presence of a cable 2. If the detector 42 detects the presence of a cable 2, the controller 24 conditions the AC signal source 16 to turn off the AC input signal 17 to prevent interference with the signal processing provided by the remainder of the system 14 (not shown).

The detector 42 may also determine the type of cable 2 in response to an amplitude dependent characteristic of the detected AC output signal 38. For example, different cables 2 have different characteristic capacitance. This results in different impedances for the AC input signal 17, and different detected amplitudes of the detected output AC signal 38. Tests may be performed on different cables 2 to determine the characteristic capacitance, and the corresponding amplitude of the detected AC output signal 38. The results of these tests may be saved in a memory 52 in the controller 24. The amplitude of a detected AC output signal 38 may be compared to the amplitudes saved in the memory 52 to determine the type of cable 2 connected to the system 14. The memory 52 may also store an AC output signal 38 value measured when the cable 2 is not connected to the cable connector 12. The detector 42 determines whether the cable 2 is connected to the cable connector 12 in response to the stored AC output signal 38 value measured when the cable 2 is not connected to the cable connector 12.

FIG. 1b illustrates another embodiment of a system 14 according to principles of the present invention. In FIG. 1b, the cable detection system 14 includes a source 16 of an input electrical AC signal 17 for coupling to a first lead of a coaxial cable 111 of a multi-lead (i.e. multiple conductor) cable 2 via a connector 12. A detector 42 is coupled to a different second lead of a coaxial cable 113 of the multi-lead cable 2 via the connector 12. The detector 42 automatically detects an electrical AC output signal 38 derived by capacitive coupling of the input electrical AC signal 17 occurring within the multi-lead cable 2 incorporating the first and second coaxial cables (111 and 113, respectively). The detector 42 further enables the determination of whether the multi-lead cable 2 is connected to the cable connector 12 in response to an amplitude dependent characteristic of the detected AC output signal 38. A controller 24 automatically initiates generation of the input electrical AC signal 17 for coupling to the first lead of coaxial cable 111, and turns off the input electrical AC signal 17 after determination by the detector 42 of whether the multi-lead cable 2 is connected to the cable connector 12.

In FIG. 1b, the first lead is one of: (a) a shield 110 of a first coaxial cable 111, and/or (b) an inner conductor 112 of a first coaxial cable 111 incorporated in the cable 2, and the second lead is one of: (a) a shield 114 of a different second coaxial cable 113, and/or an inner conductor 116 of a different second coaxial cable 113 incorporated in the cable 2.

In this embodiment, there is a capacitive coupling between the conductors of the respective coaxial cables 111 and 113. This is represented by a capacitor in phantom connected between the inner conductors 112 and 116 of the respective coaxial cables 111 and 113 respectively. One skilled in the art understands that there is a capacitive coupling among the respective conductors 110, 112, 114 and 116 of the coaxial cables 111 and 113, and understands that the impedance among these respective conductors differs. As described above with respect to FIG. 1*a*, the detector 42 may determine the type of cable in response to an amplitude dependent characteristic of the detected AC output signal 38.

FIG. 1*c* is another embodiment of a cable detection system 14 according to principles of the present invention. In FIG. 1*c*, a source 16 of an input electrical AC signal 17 may be coupled to shield conductors (110, 114, . . . 11*y*) of a plurality of leads (e.g. 111, 113, . . . 11*n*) of a multi-lead cable 2 via a connector 12. The plurality of leads (111, 113, . . . 11*n*) of the multi-lead cable 2 may be coaxial cables, and include at least one inner conductor and at least one shield. A detector 42 is also coupled to the inner conductors (112, 116, . . . 11*x*) of the plurality of leads (e.g. 111, 113, . . . 11*n*) of the multi-lead cable 2 via the connector 12. The detector 42 detects an electrical AC output signal 38 derived by capacitive coupling of the input electrical AC signal 17 occurring within the multi-lead cable 2. The detector 42 enables determination of whether the cable 2 is connected to the cable connector 12 in response to an amplitude dependent characteristic of the detected AC output signal 38. A controller 24 automatically initiates the determination of the amplitude dependent characteristic of a detected AC output signal 38 on individual ones of the inner conductors (112, 116, . . . 11*x*) of the plurality of leads (111, 113, . . . 11*n*) of the multi-lead cable 2 in response to the input electrical AC signal being applied to individual leads of the multi-lead cable 2 one at a time.

The AC input signal 17 from the AC signal source 16 is coupled to a signal input terminal of a switch 120. Respective signal output terminals of the switch 120 are coupled to corresponding shield conductors (110, 114, . . . 11*y*) of the plurality of leads (111, 113, . . . 11*n*) of the multi-lead cable 2. An output terminal of the controller 24 is coupled to a control input terminal of the switch 120. Correspondingly, respective inner conductors (112, 116, . . . 11*x*) of the plurality of leads (111, 113, . . . 11*n*) are coupled to respective signal input terminals of a switch 122. An output terminal of the switch 122 provides the AC output signal 38 and is coupled to an input terminal of the detector 42. An output terminal of the controller 24 is coupled to a control input terminal of the switch 122.

The switch 120 operates to couple the input AC signal 17 from the AC signal source 16 to a conductor of a selected one of the plurality of leads (111, 113, . . . 11*n*) in response to the value of the control signal 53 from the controller 24 to the switch 120. Concurrently, the switch 122 operates to couple a conductor of a selected one of the plurality of leads (111, 113, . . . 11*n*) to the detector 42 in response to the value of the control signal. 53 from the controller 24 to the switch 122. In this manner, the controller 24 may initiate determination of the amplitude dependent characteristic of the detected AC output signal 38 on individual ones of the plurality of leads (111, 113, . . . 11*n*) by providing appropriate control signals 53 to the switches 120 and 122.

In operation, the AC signal source 16 generates an alternating current signal 17. The alternating current signal 17 is applied to a first conductor (e.g. 110) of the multi-lead cable 2 via the switch 120. An alternating current signal at a second conductor (e.g. 112) of the multi-lead cable 2 is detected by coupling of the selected second conductor (e.g. 112) to the detector 42 via switch 122. The alternating current signal at the second conductor (e.g. 112) of the multi-lead cable 2 is detected to produce a detected signal. A proper interconnection of the multi-lead cable 2 to the cable connection 12 is identified in response to a characteristic of the detected signal. More specifically, the alternating current signal 17 is sequentially applied to the plurality of shield conductors (110, 114, . . . 11*y*) of the plurality of leads (111, 113, . . . 11*n*) of the multi-lead cable 2. The cable type is determined in response to the detected presence or absence of an inner conductor (112, 116, . . . 11*x*) of the plurality of leads (111, 113, . . . 11*n*). This may be done by associating a particular combination of leads (e.g. 111, 113, . . . 11*n*) present within the multi-lead cable 2 with a specific type of cable. After the specific type of cable has been identified, the generation of the alternating current signal is suppressed.

The detector 42 determines a type of cable connected to the system 14 in response to a plurality of measurements of amplitude dependent characteristics of the detected AC output signal 38 on a plurality of inner conductors (112, 116, . . . 11*x*) of the plurality of leads (111, 113, . . . 11*n*) of the multi-lead cable 2. For example, particular ones of the plurality of inner conductors (112, 116, . . . 11*x*) may be detected while other particular ones of the plurality of inner conductors (112, 116, . . . 11*x*) may not be detected, i.e. not be present in the multi-lead cable 2. This provides an indication of the number and arrangement of leads in the multi-lead cable 2. Further, the plurality of measurements of the amplitude dependent characteristic of the detected AC output signal 38 may be compared to predetermined sets of such measurements stored in the memory 52 to provide additional information related to the type of cable connected to the system 14.

The amplitude dependent characteristic of the detected AC output signal 38 may comprise a detected voltage substantially proportional to: (a) a peak to peak amplitude, (b) a root-mean-square amplitude, and/or (c) an average rectified amplitude value, of the detected AC output signal 38. The detector 42 determines whether a multi-lead cable 2 is connected to the cable connector 12 in response to the detected voltage exceeding a predetermined threshold value. In addition, synchronous demodulation may be employed to sense only the signal of interest, i.e. the output AC signal 38 derived from the input AC signal 17, and to reject spurious signals.

Figure 2:
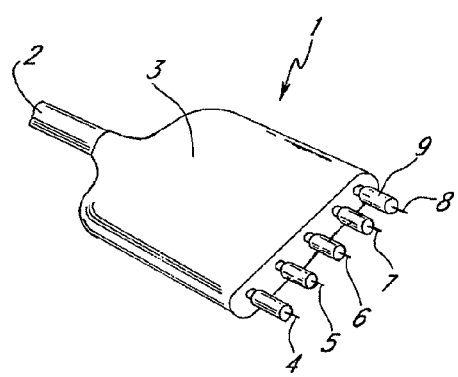
FIG. 2 is a more detailed perspective view of an exemplary electrocardiogram cable including a cable connector for interconnection to a patient monitor as utilized by the present invention.

A more detailed cable connector or plug 1 is illustrated in FIG. 2. The connector 1 serves as the termination point for a multi-conductor cable 2, the cable 2 receiving multiple power, control and data signals, for example, from an electronic device such as a patient monitor. The cable 2 is typically formed to include a plurality of coaxial cables comprising respective centrally located conductors substantially surrounded by corresponding shields. This configuration has significant inherent characteristic capacitance which is typically more easily detected than would be possible in the case of a ribbon or other non-coaxial cable.

The connector 1 includes a grip 3 that contains suitable mechanical transitions to permit individual coaxial cables within the cable 2 to be separated and the centrally located conductors terminated at individual pins, e.g. 4, 5, 6, 7 and 8. Each pin is surrounded by a shield 9. The shield 9 is connected to the shield associated with the centrally located conductor connected to the pin. The shield 9 is typically maintained at a nominal reference or ground potential. The respective shields of the plurality of coaxial cables in the cable 2 may also be interconnected to an electrically conductive jacket that surrounds the coaxial cables within the cable 2.

The cable 2 typically terminates at each end with a substantially identical connector 1. The number of pins shown is merely exemplary and the cable 2 may in practice contain either a fewer or greater number of individual conductors as may be appropriate for the particular devices being interconnected. However, the present invention is particularly advantageous when used in conjunction with a cable that has been standardized for a particular industry and where the number of conductors within the cable 2 is not only fixed, but typically all of the conductors are already dedicated to some use by the interconnected device.

Figure 3:
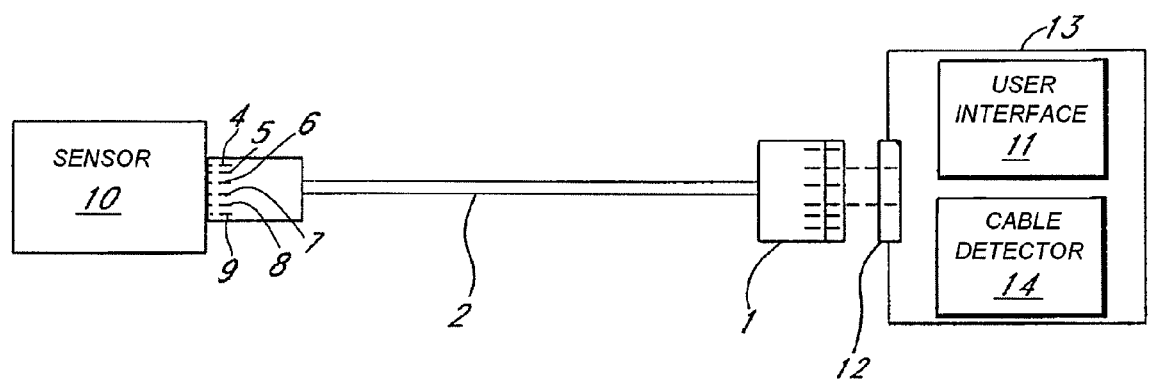
FIG. 3 is a block diagram of the interconnection between an electrocardiogram sensor, an electrocardiogram cable and a patient monitor including the cable presence detector according to principles of the present invention.

An example of a device that utilizes a multi-conductor interconnection cable 2 is the electrocardiogram sensor 10 illustrated in FIG. 3. The sensor 10 is placed into contact with the skin of a human patient in order to obtain physiological data. Alternatively, the sensor 10 may include conductors (not shown) which connect to a plurality of sensors which are placed into contact with the skin of a patient. The sensor 10 includes the cable 2 which terminates at the plug 1. The data collected by the sensor 10 is transferred to a patient monitor 13 via the cable 2, the patient monitor 13 includes a cable connector 12 which is adapted to receive the plug 1. In this manner the data generated by the sensor 10 may be suitably displayed on a display device 11 used to display a patient monitor user interface (UI). In this embodiment, the display device 11 displays ECG lead signal waveforms for inspection by medical personnel.

Figure 4:
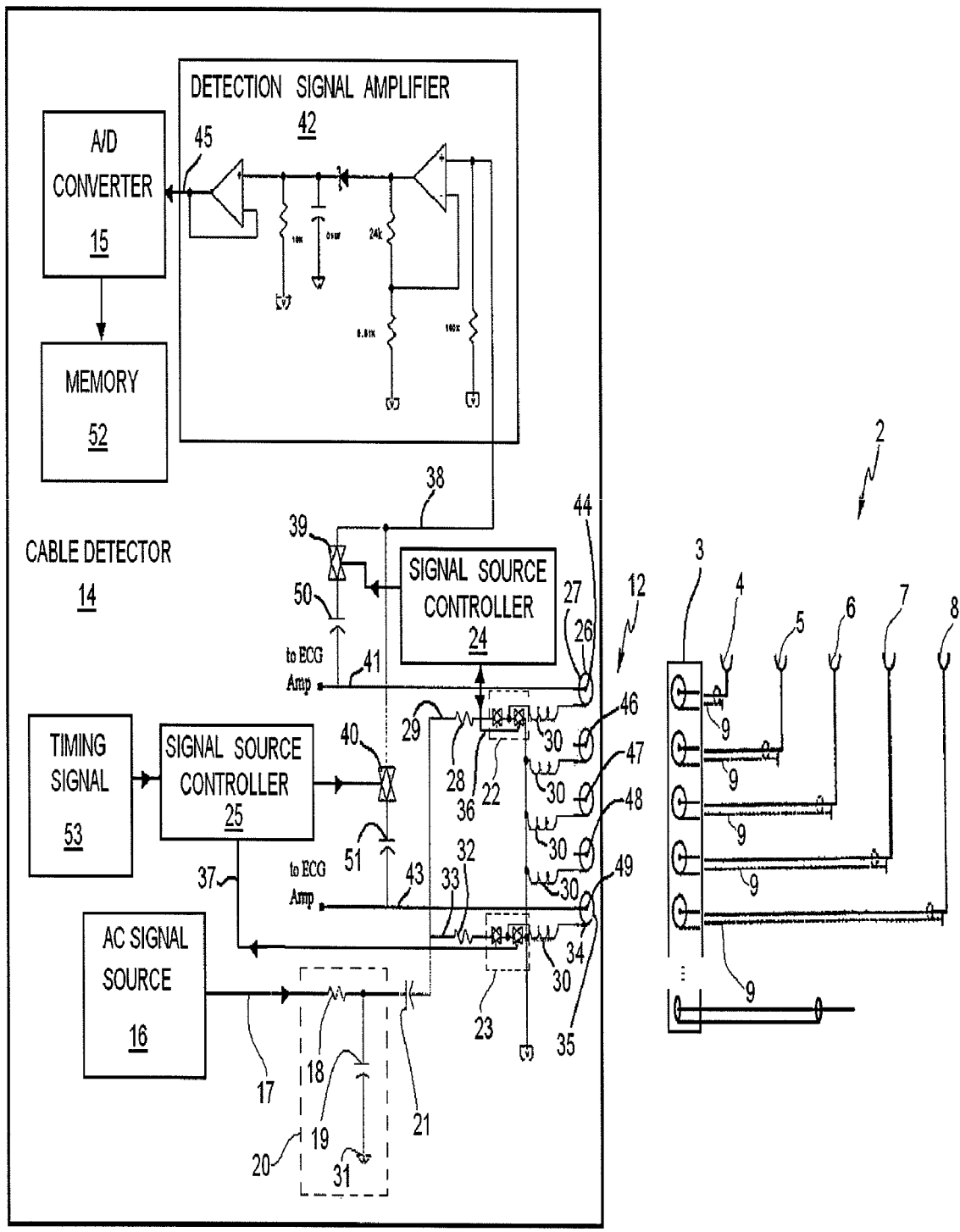
FIG. 4 is a schematic diagram of the cable detector depicted in FIG. 2.

In order to ensure the integrity and/or correct configuration of the data appearing on the user interface 11, the patient monitor 13 includes a cable detector 14. As best seen in FIG. 4, the cable detector 14 includes an alternating current signal source 16 that generates a relatively low amplitude level signal 17. Typically the signal 17 has an amplitude value of approximately three volts peak to peak, a current value of thirty three microamperes, and is generated as an approximately eighty kilohertz (kHz) sine or square wave. A typical ECG cable also carries an AC signal used for impedance measurement of respiration. The nominally eighty kHz signal 17 is selected to be approximately twice the frequency of the respiration measurement signal in order to avoid beat frequency or mixing product interference with other measurements.

The signal 17 is sent to a resistor-capacitor (RC) filter 20 that includes a resistor 18 and a capacitor 19. The nominal value of the resistor 18 is approximately three thousand ohms while the value of the capacitor is typically thirty three hundred picofarads. When processing the eighty kilohertz frequency of the signal 17, the resultant time constant of the RC filter 20 tends to make a square wave input signal 17 more sinusoidal, which is desirable in order to reduce rapid transition edge noise coupling. The signal 17 is coupled into at least one of the cable leads 4-9 via coupling capacitor 21 which has a nominal value of thirty three hundred picofarads.

The eighty kilohertz (kHz) signal 17 is interconnected to the shield conductor 9 via either a first switch 22 or a second switch 23. For example, a first signal source controller 24 automatically applies a first control signal 36 to first switch 22 to complete the circuit between the signal 17 and the socket shield 26 that is associated with the socket connector 27. The socket shield 26 is nominally at the same potential as the shield conductor 9, which is nominally at ground potential 31. A first coupling resistor 28, having a nominal value of one thousand ohms, is present in the signal path 29 and allows a relatively larger amount of current to reach the shield 26 as may be appropriate for a cable having a first, relatively lower value of inherent cable coupling (i.e. characteristic) capacitance. The first signal source controller 24 is also interconnected to a switch 39, which controls access of the signal path 41 to the detection signal amplifier 42 via a coupling capacitor 50 having a nominal value of thirty three hundred picofarads.

A second signal source controller 25, which may be integrated with the first controller 24, applies a second control signal 37 to a second switch 23 in order to complete the circuit between the signal 17 and the socket shield 34 that is associated with the socket connector 35. The socket shield 34 is nominally at the same potential as the shield conductor 9, which is nominally at ground potential 31. A second coupling resistor 32, having a nominal value of approximately one thousand ohms, is present in signal path 33 and allows a relatively smaller amount of current to reach the shield 34 as may be appropriate for a cable having a second, relatively higher value of inherent cable coupling capacitance. A radio frequency choke 30, having a nominal value of sixty eight hundred microhenries, serves to attenuate any higher frequency signal energy which may be coupled into the shield conductor 9. The second signal source controller 25 is also interconnected to a switch 40, which controls access of the signal path 43 to the detection signal amplifier 42 via a coupling capacitor 51 having a nominal value of thirty three hundred picofarads. While interconnections to socket connectors 27 and 35 are shown for clarity, the controllers 24 and 25 may be connected to the respective shields associated with pins 44 and 46-49. The signal source controllers 24, are therefore capable of selecting the connector pins in the patient monitor cable socket 12 as needed. A timing signal 53, which may be interconnected to one or both controllers 24 and 25, synchronizes the generation and suppression of the AC signal 17 when the presence of signal 17 would cause harmful interference to other signals being received or processed by the patient monitor 13.

In operation, the signal 17 is coupled to one of the shield conductors 9 of the cable 2, creating a relatively larger detection signal 38 by completing the circuit through another of the cable leads, if and when the cable 2 is properly plugged into the patient monitor 13. The detection signal 38 is relatively smaller when the cable 2 is absent. The additional amplitude of the detection signal 38 when the cable 2 is present is proportional to the inherent capacitance between the cable leads within cable 2 and is used to distinguish between the cable 2 being present or not being present. For example, a typical patient monitor cable 2 has a nominal interelectrode capacitance of one hundred pf. Thus a given patient monitor connector pin 44 will be loaded by more than one hundred pf capacitance value if the cable 2 is properly inserted.

The resulting detected signal voltage 38 that is detected on the signal lead 44, for example is buffered, rectified and filtered by the signal detection amplifier 42 in order to produce a processed output signal 45. Synchronous detection or demodulation may be employed by the signal detection amplifier 42 when the detection signal 38 includes a noise or other spurious signal component, or an actual sensor data or excitation signal such as may occur in the case of electrocardiogram, respiration or blood oxygen saturation signals.

The processed signal 45 is sent to an analog to digital (A/D) converter 15 that is typically already a part of the patient monitor 13 (FIG. 3) in order to permit additional software processing and to enable the appropriate data presentation on the patient monitor display device 11. The processed signal 45 typically has an amplitude voltage characteristic that is substantially proportional to a peak to peak amplitude value, a root-mean-square value and/or an average rectified value. In a preferred embodiment, the processed signal 45 has a value of at least three hundred millivolts when the cable 2 is present and a value of approximately one millivolt when the cable 2 is absent. Thus a threshold value in excess of the three hundred millivolts will trigger signal processing software within the patient monitor 13 to recognize the presence of a properly connected cable 2.

An initial baseline value of the capacitively coupled eighty kHz signal 38 amplitude in the absence of the sensor cable 2 is stored in memory 52 and is therefore available to be subtracted from the absolute amplitude of the detected signal 38, thereby providing a relatively more accurate comparison of the value of the detected signal 38 for the cable present versus cable absent states. After the cable detection process is completed, the eighty kHz signal source 16 is turned off by the controllers 24 and/or 25 in order to reduce interference with the actual sensor data, such as ECG and respiration detection, which typically utilize the same cable conductors.

In operation, one connector pin 44, 46, 47, 48 or 49 is examined at a given time, being selected by a signal from the signal source controllers 24 and 25. When the cable 2 is a typical ECG cable, it may be one of four different types, where the number of conductors may be three, five six or twelve, respectively. The electrodes are placed at various standard points on the patient's body to provide electrode lead data with designations such as V1, V2, V3, V4, V5, V6, RA, LA and LL, with an additional lead being connected to system ground, which is typically the patient's right leg. Some of the electrode designations are present in cables having a given number of conductors. A twelve conductor cable, for example, is the only cable 2 that contains the V1 lead, while a six conductor cable is the only cable that contains the V5 lead without a V1 lead. A five conductor cable contains the V2 lead without the V1 or V5 lead, while a two conductor cable contains only the RA lead without the other leads being present. Thus only one ECG pin (e.g. RA, V2, V5, and V1) from each of the four (3, 5, 6, or 12 lead) possible types of ECG cables needs to be tested. A combination of the four cable detected signals allows determination of which type of ECG cable is connected to the patient monitor 13 and enables the appropriate ECG display and monitoring function, including the configuration of the ECG display, to be selected by any patient monitor software.

While the invention has been described with reference to a specific embodiment, various modifications may be made. In particular, the controllers 24 and 25 may be hardware, combined into a single device or electronic element, or implemented partially or entirely by software. The frequency of the signal source 16 may be other than eighty kHz, and in some cases may be modulated in order to determine additional characteristics of the cable 2 or the integrity of the connection to the socket 12. The signal source 16 may introduce the signal 17 at the center conductor of a cable or at the shield, and various intervening components may be present in addition to those illustrated in the figures. While an ECG cable 2 has been disclosed in the preferred embodiment, many types of industry standard cables may be used and the number and arrangement of conductors automatically determined based on the detection of the presence or absence of a conductor at certain standard, identifiable pins locations.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. A cable detection system, comprising:
a source of an input electrical AC signal for coupling to a first lead pin of a cable connector and providing the input electrical AC signal to the first lead pin; and
a detector coupled to a different second lead pin of said cable connector that detects an electrical AC output signal derived by capacitive coupling of the input electrical AC signal occurring within a multi-lead cable at the second lead pin and compares an amplitude dependent characteristic of said detected AC output signal with a predetermined threshold value to determine whether said multi-lead cable is connected to said cable connector and said detector determines a type of said multi-lead cable in response to the amplitude dependent characteristic of said detected AC output signal.

2. The system of claim 1 including a controller for automatically initiating generation of said input electrical AC signal for coupling to said first lead and for turning off said input electrical AC signal after determination by said detector of whether said multi-lead cable is connected to said cable connector.

3. A system according to claim 1, wherein:
said first lead is a shield of a coaxial cable and
said second lead is an inner conductor of said coaxial cable.

4. A system according to claim 1, wherein:
said second lead is a shield of a coaxial cable and
said first lead is an inner conductor of said coaxial cable.

5. A system according to claim 1, wherein:
said first lead is at least one of, (a) a shield of a first coaxial cable and (b) an inner conductor of a first coaxial cable incorporated in said multi-lead cable and
said second lead is at least one of, (c) a shield of a different second coaxial cable and (d) an inner conductor of a different second coaxial cable incorporated in said multi-lead cable.

6. A system according to claim 1, further comprising:
a memory for storing an AC output signal value measured when said multi-lead cable is not connected to said connector; wherein:
said detector determines whether said multi-lead cable is connected to said cable connector in response to said stored AC output signal value measured when said multi-lead cable is not connected to said connector.

7. A system according to claim 1, wherein said detector determines whether said multi-lead cable is connected to said cable connector in response to an amplitude dependent characteristic of said detected AC output signal exceeding a predetermined threshold value.

8. A system according to claim 1, further comprising a controller for automatically synchronizing initiating generation of said input electrical AC signal for coupling to said first lead and detection by said detector of whether said multi-lead cable is connected to said cable connector in response to a timing signal to avoid interference with other signals.

9. A system according to claim 1, wherein said amplitude dependent characteristic of said detected AC output signal comprises a detected voltage substantially proportional to at least one of, (a) a peak to peak amplitude, (b) a root-mean-square and (c) an average rectified value, value of said detected AC output signal and said detector determines whether said multi-lead cable is connected to said cable connector in response to said detected voltage exceeding a predetermined threshold value.

10. A system according to claim 1 wherein synchronous demodulation is employed to sense only the signal of interest and to reject spurious signals.

11. A cable detection system, comprising:
a source of an input electrical AC signal for coupling to a first coaxial lead of a cable via a connector and providing the input electrical AC signal to the first coaxial lead;
a detector coupled to a different second coaxial lead of said cable via said connector that automatically detects an electrical AC output signal derived by capacitive coupling of the input electrical AC signal occurring within the cable at the second coaxial lead and compares an amplitude dependent characteristic of said detected AC output signal with a predetermined threshold value to determine whether said cable is connected to said cable connector; and a controller that automatically initiates generation of said input electrical AC signal for coupling to said first lead and for turning off said input electrical AC signal after determination by said detector of whether said cable is connected to said cable connector and said detector determines a type of said cable in response to the amplitude dependent characteristic of said detected AC output signal.

12. A cable detection system, comprising:

a source of an input electrical AC signal for coupling to a plurality of leads of a multi-lead cable via a connector and providing the input electrical AC signal to a first lead; and a detector, coupled to a plurality of leads of said multi-lead cable via said connector, that detects an electrical AC output signal derived by capacitive coupling of the input electrical AC signal occurring within said multi-lead cable and compares an amplitude dependent characteristic of said detected AC output signal with a predetermined threshold value to determine whether said multi-lead cable is connected to said connector; and a controller that automatically initiates determination of said amplitude dependent characteristic of a detected AC output signal on individual ones of a plurality of leads of said multi-lead cable, in response to said input electrical AC signal being applied to individual leads of a plurality of leads of said multi-lead cable one at a time and said detector determines a type of said cable in response to the amplitude dependent characteristic of said detected AC output signal.

13. A system according to claim 12, wherein said plurality of leads of said multi-lead cable include at least one inner conductor and at least one shield (9) of a coaxial cable.

14. A method of identifying proper interconnection of a multiple conductor cable to a cable connector, comprising the steps of:

generating an alternating current signal;

applying the alternating current signal to a first conductor of the cable;

detecting the alternating current signal at a second conductor of the cable to produce a detected signal;

comparing a characteristic of the detected signal with a predetermined threshold value; and identifying a proper interconnection of the multiple conductor cable and the cable connector based on the comparison;

sequentially applying the alternating current signal to a plurality of conductors of the cable; and determining a cable type in response to an amplitude dependent characteristic of the detected AC output signal.

15. The method of claim 14, further comprising the step of determining a display configuration in response to the determined cable type.

16. The method of claim 14, further comprising the step of associating a particular combination of conductors within the cable with a specific type of cable.

17. The method of claim 16, further comprising the step of suppressing generation of the alternating current signal after the specific type of cable has been identified.

* * * * *